United States Patent
Guinan et al.

(10) Patent No.: US 7,083,639 B2
(45) Date of Patent: Aug. 1, 2006

(54) STENT DELIVERY CATHETER WITH GROOVED BALLOON AND METHODS OF MAKING SAME

(75) Inventors: Terry A. Guinan, Galway (IE); Tom Feeney, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 09/965,473

(22) Filed: Sep. 26, 2001

(65) Prior Publication Data

US 2003/0060832 A1    Mar. 27, 2003

(51) Int. Cl.
    *A61F 2/06*    (2006.01)
(52) U.S. Cl. ........................ 623/1.1; 606/194
(58) Field of Classification Search ........... 623/1.11, 623/1.12; 606/191–195
    See application file for complete search history.

(56) References Cited

U.S. PATENT DOCUMENTS

| 3,810,474 | A | * | 5/1974 | Cross ..................... 604/916 |
|---|---|---|---|---|
| 5,074,845 | A | | 12/1991 | Miraki et al. |
| 5,163,989 | A | | 11/1992 | Campbell et al. |
| 5,295,959 | A | | 3/1994 | Gurbel et al. |
| 5,308,356 | A | | 5/1994 | Blackshear, Jr. et al. |
| 5,320,605 | A | * | 6/1994 | Sahota ..................... 606/194 |
| 5,352,199 | A | | 10/1994 | Tower |
| 5,409,495 | A | | 4/1995 | Osborn |
| 5,445,646 | A | | 8/1995 | Euteneuer et al. |
| 5,484,411 | A | * | 1/1996 | Inderbitzen et al. ........ 606/194 |
| 5,545,132 | A | | 8/1996 | Fagan et al. |
| 5,620,457 | A | | 4/1997 | Pinchasik et al. |
| 5,728,068 | A | * | 3/1998 | Leone et al. ............... 623/1.11 |
| 5,836,965 | A | | 11/1998 | Jendersee et al. |
| 5,910,102 | A | * | 6/1999 | Hastings .................... 600/3 |
| 5,913,871 | A | | 6/1999 | Werneth et al. |
| 5,935,135 | A | | 8/1999 | Bramfitt et al. |
| 6,022,359 | A | | 2/2000 | Frantzen |
| 6,027,510 | A | | 2/2000 | Alt |
| 6,048,350 | A | | 4/2000 | Vrba |
| 6,056,906 | A | * | 5/2000 | Werneth et al. ............ 264/135 |
| 6,059,713 | A | * | 5/2000 | Urick et al. ................ 600/3 |
| 6,254,608 | B1 | * | 7/2001 | Solar ........................ 606/194 |
| 6,280,412 | B1 | * | 8/2001 | Pederson et al. .......... 606/108 |
| 6,293,959 | B1 | * | 9/2001 | Miller et al. ............... 606/194 |
| 6,302,893 | B1 | * | 10/2001 | Limon et al. ............. 623/1.11 |
| 6,464,718 | B1 | * | 10/2002 | Miller et al. ............... 623/1.11 |
| 2002/0120321 | A1 | | 8/2002 | Gunderson et al. |

FOREIGN PATENT DOCUMENTS

EP    1132059 A1    9/2001

* cited by examiner

*Primary Examiner*—Eduardo C. Robert
*Assistant Examiner*—Jessica R. Baxter

(57) ABSTRACT

A stent-delivery catheter includes a balloon having an intermediate body, tapered end portions and at least one circumferential groove adjacent a transition between the intermediate body and a tapered end portion. While the balloon is deflated, the groove allows the tapered end portion of the balloon to function as a dam to retain a stent on the balloon. This abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

20 Claims, 2 Drawing Sheets

STENT DELIVERY CATHETER WITH GROOVED BALLOON AND METHODS OF MAKING SAME

FIELD OF THE INVENTION

The invention relates to intraluminal stenting, and in particular, to a catheter having a grooved stent delivery balloon.

BACKGROUND OF THE INVENTION

Intraluminal stenting is useful in treating tubular vessels in the body which are narrowed or blocked and it is an alternative to surgical procedures that intend to bypass such an occlusion. When used in endovascular applications, the procedure involves inserting a prosthesis into an artery and expanding it to prevent collapse of the vessel wall.

Percutaneous transluminal angioplasty (PTCA) is used to open coronary arteries which have been occluded by a build-up of cholesterol fats or atherosclerotic plaque. Typically, a guide catheter is inserted into a major artery in the groin and is passed to the heart, providing a conduit to the ostia of the coronary arteries from outside the body. A balloon catheter and guidewire are advanced through the guiding catheter and steered through the coronary vasculature to the site of therapy. The balloon at the distal end of the catheter is inflated, causing the site of the stenosis to widen. Dilation of the occlusion, however, can form flaps, fissures or dissections which may threaten re-closure of the dilated vessel. Implantation of a stent can provide support for such flaps and dissections and thereby prevent reclosure of the vessel. Reducing the possibility of restenosis after angioplasty reduces the likelihood that a secondary angioplasty procedure or a surgical bypass operation will be necessary.

A stent is typically a hollow, generally cylindrical device formed from wire(s) or a tube and the stent is commonly intended to act as a permanent prosthesis. A stent is deployed in a body lumen from a radially contracted configuration into a radially expanded configuration which allows it to contact and support a body lumen. The stent can be made to be either radially self-expanding or expandable by the use of an expansion device. The self expanding stent is made from a resilient material while the device-expandable stent is made from a material which is plastically deformable. A plastically deformable stent can be implanted during an angioplasty procedure by using a balloon catheter bearing the compressed stent which has been loaded onto the balloon. The stent radially expands as the balloon is inflated, forcing the stent into contact with the body lumen, thereby forming a support for the vessel wall. Deployment is effected after the stent has been introduced percutaneously, transported transluminally and positioned at a desired location by means of the balloon catheter.

A balloon of appropriate size and pressure is first used to open the lesion. The process can be repeated with a stent loaded onto a balloon. Direct stenting involves simultaneously performing angioplasty and stent implantation using a stent mounted on a dilatation balloon. After the balloon is withdrawn, the stent remains as a scaffold for the injured vessel.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1:
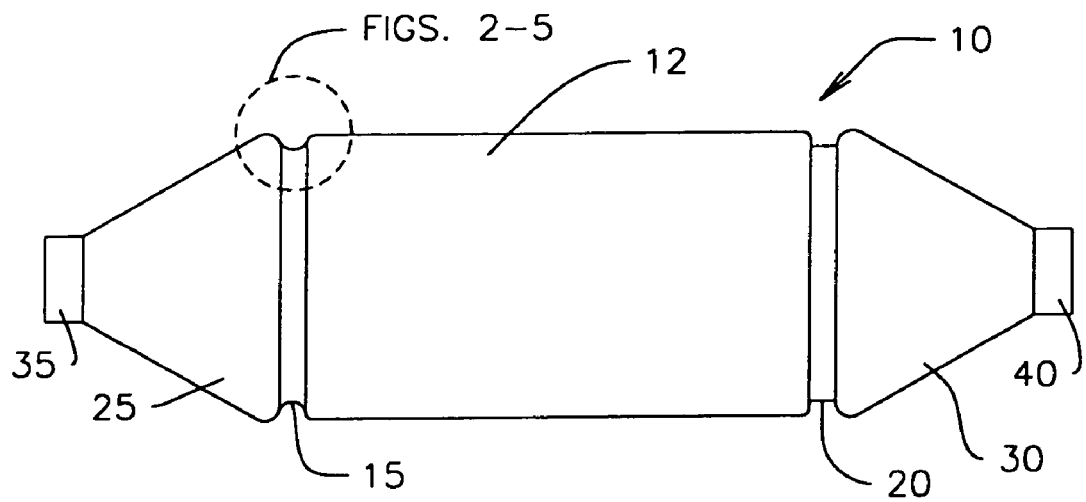
FIG. 1 is a longitudinal view of a balloon in accordance with the invention.
Figure 6:
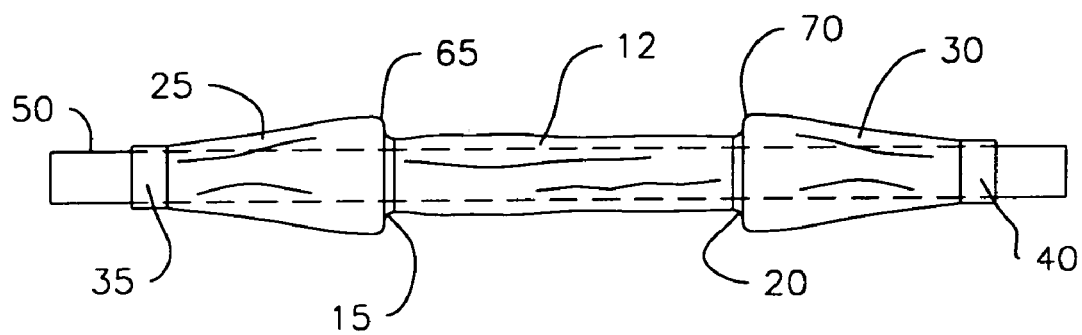
FIG. 6 is a longitudinal view of a balloon catheter in accordance with the invention, shown with the balloon deflated.

Applicant's invention is useful with any expandable stent, such as those stents designed for delivery by a balloon. The stent may be generally cylindrical, and it may be mounted on a tubular balloon. FIG. 1 shows balloon 10, which can retain a stent thereon during delivery. Proximal and distal circumferential grooves 15, 20, respectively, surround balloon 10 adjacent the transitions between intermediate body 12 and proximal and distal cones 25, 30, respectively. Intermediate body 12 may be generally cylindrical in shape, and it may be centrally located between proximal and distal cones 25, 30. Proximal and distal cones 25, 30 terminate in proximal and distal ends 35, 40, respectively, which are adapted to be mounted on catheter shaft 50, as shown in FIG. 6.

Figure 2:
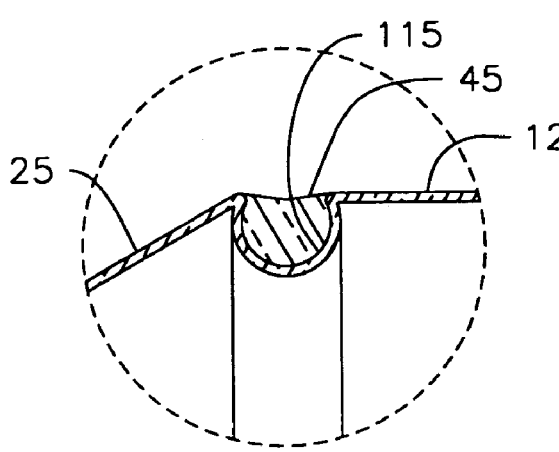
FIGS. 2–5 are enlarged, longitudinal portions (FIGS. 2, 4 and 5 in section) of balloons in accordance with the invention, showing several alternative embodiments of circumferential grooves.

In FIG. 1, proximal circumferential groove 15 is substantially U-shaped when viewed in longitudinal section, and the diameters of balloon 10 measured distal and proximal to groove 15 are substantially equal. Distal circumferential groove 20 is an alternative embodiment to groove 15 and is flat-bottomed, or rectangular in longitudinal section. FIGS. 2–5 show several other alternative embodiments of circumferential grooves in balloon 10. As shown in FIG. 2, circumferential groove 115 is substantially C-shaped in longitudinal section. Groove 115 may also be described as being generally circular in longitudinal section, with an open arc portion. Groove 115 is also shown as being optionally filled with flexible material 45. Any of the circumferential grooves in the invention may be partially or fully filled with flexible material 45, as will be described further below.

Figure 3:
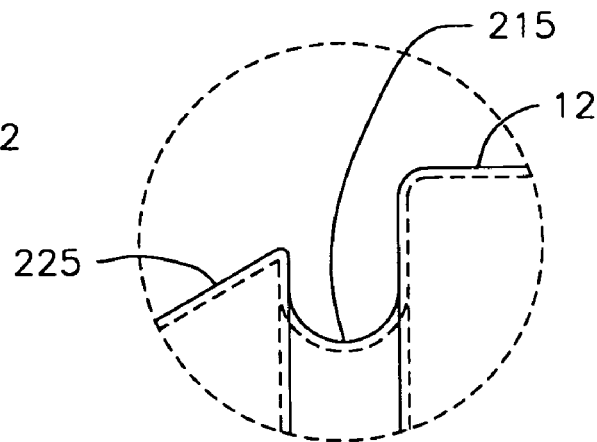

As shown in FIG. 3, circumferential groove 215 is substantially U-shaped. in longitudinal section. However, groove 215 is located toward the cone side of the transition between cylindrical intermediate body 12 and cone 225, such that the diameters of balloon 10 measured distal and proximal to groove 215 are substantially unequal.

Figure 4:
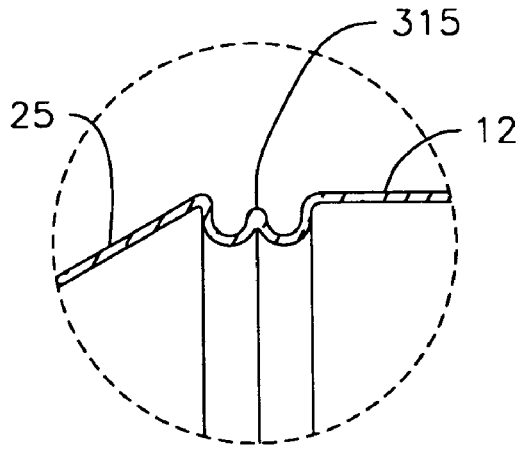
Figure 5:
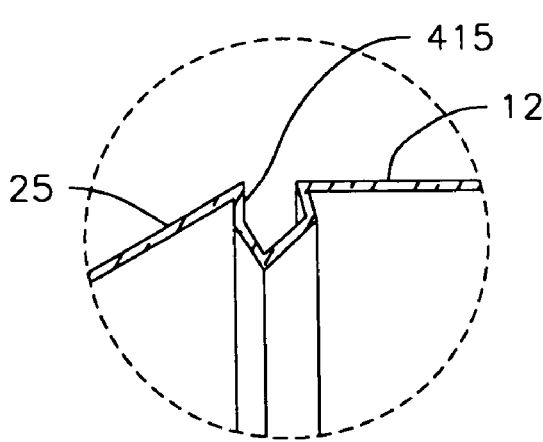

As shown in FIG. 4, circumferential groove 315 is substantially W-shaped in longitudinal section. Groove 315 may also be considered as two U-shaped circumferential grooves formed adjacent each other. As shown in FIG. 5, circumferential groove 415 is, in longitudinal section, a polygon with an open side.

Balloon 10 can be made according to stretch blow molding processes that are well known to those skilled in the arts of dilatation and stent delivery balloons. Molds used in balloon forming typically have hollow intermediate sections with removable end inserts for forming cones, and are made of metal such as brass. In known alternatives, balloon molds may be unitary tubular chambers that have been thermoformed of a high temperature material such as glass. Circumferential grooves 15, 20, and their alternatives shown herein can be formed during conventional stretch blow molding, thus providing a generally uniform wall thickness throughout the balloon regions that include grooves 15, 20.

A balloon mold can be adapted in a variety of ways to form balloon 10 with circumferential grooves 15, 20. In a first example, ring members may be inserted inside a balloon mold such that balloon 10 forms around the ring members to create circumferential grooves 15, 20. The ring members can be cast, molded or machined of any material that will retain its shape during balloon forming, such as a metal, a ceramic, a thermoset polymer or a thermoplastic having a sufficiently high melting temperature. A conventional multi-part mold may have one or more internal grooves adapted to retain the ring members in the desired position within the mold. For instance, ring retaining grooves may be machined adjacent the interface between a mold center section and the mating removable inserts. In a second example, a unitary glass balloon mold (see U.S. Pat. No. 5,163,989) can be formed to capture the ring members within the inner chamber. Balloon 10 can be made from single or multiple layers of thermoplastics such as polyolefins, polyurethanes, polyamides, blends or block copolymers that include these materials, or other polymers known to be suitable for dilatation and stent delivery balloons.

Circumferential grooves 15, 20 create a partial mechanical disengagement between balloon intermediate body 12 and cones 25, 30. The partial disengagement permits adjacent body 12 and cones 25, 30 to move differently in the radial direction, comparable to the way a rolling diaphragm works in the axial direction. For example, if intermediate body 12 is radially restrained during inflation of balloon 10, then circumferential grooves 15, 20 will allow a limited radial expansion of cones 25, 30, thus creating radial steps at both ends of intermediate body 12. These radial steps can be heat set into balloon 10, and can act as dams to prevent stent 60 from sliding off of balloon 10.

Any of the circumferential grooves disclosed herein can be partially or completely filled with flexible material 45, as mentioned above. The addition of such a material to a circumferential groove can reinforce or enhance the dam effect created by the radial steps at the ends of intermediate body 12. Substances selected for flexible material 45 may be elastic or inelastic, thermoplastic or thermoset polymers, and may be foamed to enhance flexibility. Flexible material 45 may also comprise a formulation typically used for coating medical devices, including balloons, to either reduce or enhance friction properties. Elastic or elastomeric materials may provide a high coefficient of friction relative to the material of balloon 10, thus enhancing stent retention thereon. To avoid separation between flexible material 45 and balloon 10, material 45 should be adhered to balloon 10, either by inherent adhesive properties of the material, or by a separate bonding component.

Figure 7:
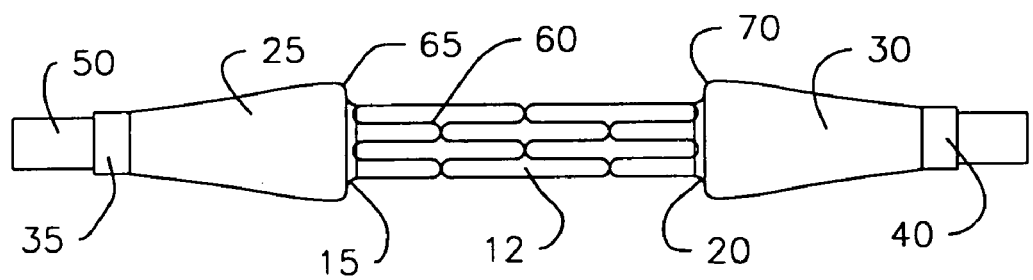
FIG. 7 is a longitudinal view of a stent delivery balloon catheter in accordance with the invention, shown with a stent mounted thereon and the balloon deflated.
Figure 8:
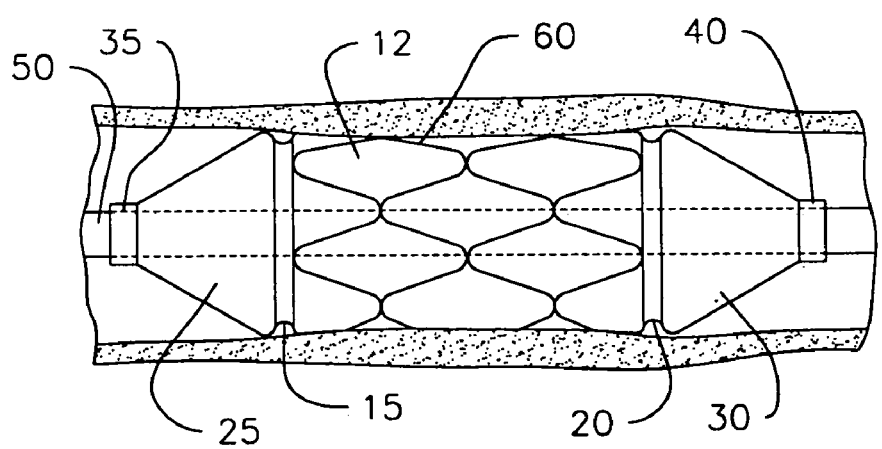
FIG. 8 shows the embodiment of FIG. 7 wherein the balloon has been inflated to deliver the stent in a vessel of a patient.

FIG. 7 shows a stent delivery balloon catheter in accordance with the invention, and which has been made as follows. Balloon 10 is mounted on catheter shaft 50. Balloon 10 is deflated about shaft 50, and stent 60 is crimped or compressed about intermediate body 12. With stent 60 held in the radially compressed configuration, inflation pressure is applied to balloon 10. In response to this internal pressure, circumferential grooves 15, 20 allow limited expansion of cones 25, 30 to form proximal and distal steps 65, 70, respectively. Heat setting of balloon 10 imparts thereto a memory of the shapes of steps 65, 70. Heat setting can be performed with or without internal pressure in balloon 10.

Alternatively, steps 65, 70 may be formed after deflation of balloon 10 by wrapping balloon 10 around shaft 50 and crimping stent 60 around intermediate body 12. During stent crimping, circumferential grooves 15, 20 allow cones 25, 30 to retain a larger deflated profile than that of intermediate body 12. In this way, steps 65, 70 can be formed without pressurizing balloon 10.

The invention may be practiced with one or more circumferential grooves adjacent the ends of intermediate body 12 of balloon 10. For example, a single groove 20 may be formed in balloon 10 adjacent the transition between intermediate body 12 and distal cone 30. Alternatively, a single groove 15, may be formed in balloon 10 adjacent the transition between intermediate body 12 and proximal cone 25. As shown in FIG. 4, two or more grooves may be formed next to each other adjacent a transition between intermediate body 12 and a cone. Any combinations of alternative embodiments of circumferential grooves are also possible, with or without flexible filler materials.

We claim:

1. A balloon adapted to be mounted on a catheter and to receive a stent having proximal and distal ends, the balloon comprising:
    proximal and distal cones,
    proximal and distal ends, respectively adjacent to the proximal and distal cones, and adapted for being mounted to the catheter,
    an intermediate body between the proximal and distal cones and configured to receive a stent thereon, the intermediate body having a proximal region configured to receive the stent proximal end, and a distal region configured to receive the stent distal end, and
    at least one circumferential groove formed on the balloon wall between one of the intermediate body proximal and distal regions and the respective proximal and distal cone for mechanically disengaging the respective cone from the intermediate body allowing each to move differently in a radial direction,
    wherein said at least one circumferential groove is present when the balloon is in both an inflated state and a deflated state, and imparts a smaller diameter to the balloon than does the intermediate body when the balloon is in the inflated state.

2. The balloon of claim 1, wherein the at least one circumferential groove has a shape, in longitudinal cross-section, selected from C-shapes, U-shapes, W-shapes, open-sided polygons, and combinations thereof.

3. The balloon of claim 1, wherein the at least one circumferential groove is formed adjacent at least one of the proximal and distal cones such that balloon diameters measured distal and proximal to the at least one circumferential groove are unequal.

4. The balloon of claim 1, wherein the at least one circumferential groove is at least partially filled with a flexible material that is adhered to the balloon.

5. The balloon of claim 4, wherein the flexible material comprises foamed material.

6. The balloon of claim 1 further comprising at least a second circumferential groove formed in the balloon wall between the other of the proximal end and distal end of the stent and the other of said proximal and distal cone for mechanically disengaging the other cone from the intermediate body.

7. A catheter comprising:
    an elongate shaft having a lumen there through; and a balloon adapted to receive a stent having proximal and distal ends, and mounted about a distal region of the shaft in fluid communication with the lumen, the comprising:
an intermediate body for receiving the stent thereon, the intermediate body having a proximal region configured to receive the stent proximal end, and a distal region configured to receive the stent distal end,
proximal and distal cones,
proximal and distal ends, respectively adjacent to the proximal and distal cones, and attached to the shaft,
proximal and distal transitions between the intermediate body proximal and distal regions and the proximal and distal cones, respectively, and
a distal circumferential groove formed adjacent the distal transition, the distal circumferential groove mechanically disengaging the distal cone from the intermediate body allowing each to move differently in a radial direction,
wherein said distal circumferential groove is present when said balloon is in both an inflated state and a deflated state, and imparts a smaller diameter to the balloon than does the intermediate body when the balloon is in the inflated state.

8. The catheter of claim 7 further comprising a proximal circumferential groove formed on the balloon wall adjacent the proximal transition.

9. The catheter of claim 8, wherein the balloon is capable of being partially inflated around the shaft such that the proximal and distal cones each have partially inflated profiles that are larger than a deflated profile of the intermediate body.

10. The catheter of claim 9, wherein during balloon inflation, the proximal and distal circumferential grooves form proximal and distal steps in diameter, respectively, between the deflated profile of the intermediate body and the partially inflated profiles of the proximal and distal cones.

11. A stent delivery catheter comprising:
an elongate shaft having a lumen there through, and having a distal region;
a balloon expandable stent, mounted about said intermediate body, and having proximal and distal ends; and
a balloon mounted about a the distal region of the shaft and being in fluid communication with the lumen, the balloon comprising,
an intermediate body on which the stent is mounted,
proximal and distal cones,
proximal and distal ends, respectively adjacent to the proximal and distal cones, and attached to the shaft, and
a first circumferential groove formed between one of the proximal and distal ends of the stent and a respective one of the proximal and distal cones such that the first circumferential groove mechanically disengages the one of the respective proximal and distal cones from the respective proximal and distal ends of the stent allowing each to move differently in a radial direction,
wherein said first circumferential groove is present when the balloon is in both an inflated state and a deflated state, and imparts a smaller diameter to the balloon than does the intermediate body when the balloon is in the inflated state.

12. The stent delivery catheter of claim 11 further comprising a second circumferential groove formed of the balloon wall adjacent a transition between the other of the proximal and distal ends of the stent and the other of the proximal and distal cones.

13. The stent delivery catheter of claim 12, wherein, when the balloon is deflated, the proximal and distal cones each have partially inflated profiles that are larger than a deflated profile of the intermediate body such that the proximal and distal cones form proximal and distal dams, respectively, to retain the stent on the balloon.

14. The stent delivery catheter of claim 11, wherein the first circumferential groove is at least partially filled with a flexible material that is adhered to the balloon.

15. The stent delivery catheter of claim 14, wherein the flexible material forms a first dam to help retain the stent on the balloon.

16. A method of making a stent delivery catheter comprising:
providing a catheter having an elongate shaft with a lumen there through;
mounting a balloon about a distal region of the shaft and in fluid communication with the lumen, the balloon having a flexible wall comprising an intermediate body, proximal and distal cones, and proximal and distal ends that are respectively adjacent to the proximal and distal cones and attached to the catheter shaft;
forming at least one circumferential groove on the balloon wall between the intermediate body and one of the proximal and distal cones, the at least one circumferential groove mechanically disengaging the one of the proximal and distal cones from the intermediate body allowing each to move differently in a radial direction wherein said at least one circumferential groove is present is in both an inflated state and a deflated state, and imparts a smaller diameter to the balloon than does the intermediate body when the balloon is in the inflated state;
collapsing the balloon around the catheter shaft; and
mounting a balloon expandable stent in a radially compressed configuration around the intermediate body of the balloon.

17. The method of claim 16, wherein mounting the stent further comprises holding the stent in the radially compressed configuration while inflating the proximal and distal cones to create dams to retain the stent on the balloon.

18. The method of claim 17 further comprising:
heat setting the balloon to produce a shape memory therein of the dams formed in the proximal and distal cones.

19. The method of claim 16 further comprising:
at least partially filling the at least one circumferential groove with a flexible material that is adhered to the balloon.

20. The method of claim 16 wherein the step of forming is performed prior to the step of mounting.

* * * * *